United States Patent [19]

Böger et al.

[11] Patent Number: 4,897,424

[45] Date of Patent: Jan. 30, 1990

[54] ARYLOXYPHENYLTHIOUREAS, ARYLOXYPHENYLISOTHIOUREAS AND ARYLOXYPHENYLCARBODIIMIDES AND PESTICIDAL COMPOSITIONS CONTAINING THEM

[75] Inventors: Manfred Böger, Weil am Rhein, Fed. Rep. of Germany; Jozef Drabek, Oberwil; Josef Ehrenfreund, Allschwil, both of Switzerland

[73] Assignee: Ciba-Geigy Corporation, Ardsley, N.Y.

[21] Appl. No.: 205,260

[22] Filed: Jun. 9, 1988

[30] Foreign Application Priority Data

Jun. 18, 1987 [CH] Switzerland .................. 2302/87

[51] Int. Cl.$^4$ ........................... A61K 31/155
[52] U.S. Cl. .................... 514/638; 564/254; 564/26; 564/430; 514/558; 558/4; 558/17
[58] Field of Search .................. 564/252; 514/638

[56] References Cited

U.S. PATENT DOCUMENTS

| | | | |
|---|---|---|---|
| 3,931,201 | 1/1976 | Johnston | 260/294.8 |
| 4,328,247 | 5/1982 | Drabek et al. | 424/326 |
| 4,404,225 | 9/1983 | Boger et al. | 157/09 |
| 4,734,433 | 3/1988 | Drabek | 514/508 |
| 4,812,466 | 3/1989 | Boger et al. | 514/351 |

FOREIGN PATENT DOCUMENTS 3212104 10/1983 Fed. Rep. of Germany .
1425789 2/1976 United Kingdom .

OTHER PUBLICATIONS

Chemical Abstract, vol. 100, (1984), p. 425, 100:342685.

*Primary Examiner*—James H. Reamer

*Attorney, Agent, or Firm*—Kevin T. Mansfield; Edward McC. Roberts

[57] ABSTRACT

Novel substituted aryloxyphenyl-thioureas, -isothioureas and -carbodiimides of formula I

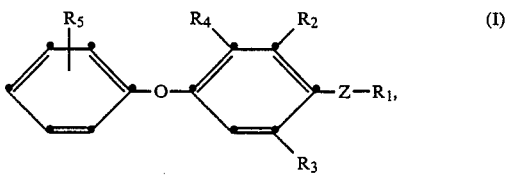

in which $R_1$ represents $C_1$-$C_{12}$alkyl, $C_1$-$C_{12}$alkyl mono- or polysubstituted by halogen and/or by $C_1$-$C_6$alkoxy, $C_3$-$C_8$cycloalkyl, $C_3$-$C_8$cycloalkyl mono- or polysubstituted by $C_1$-$C_3$alkyl, or $C_3$-$C_8$cycloalkyl-$C_1$-$C_4$alkyl;

$R_2$ represents hydrogen or $C_1$-$C_5$alkyl;

$R_3$ represents a $C_1$-$C_5$alkyl or $C_5$-$C_6$cycloalkyl;

$R_4$ represents hydrogen or methyl;

$R_5$ represents a $-(CH=CH)_2-$, $-(CH_2)_3-$ or $-(CH_2)_4-$ bridge in the 2,3- or 3,4-position;

Z represents $-NH-CS-NH-$, $-N=C(SR_6)-NH-$ or $-N=C=N-$ and $R_6$ represents $C_1$-$C_{10}$alkyl or allyl, and the salts thereof with organic or inorganic acids, processes and intermediates for their preparation, their use in the control of pests, and pesticidal compositions that contain at least one compound of formula I as active ingredient are disclosed. The preferred field of use is the control of pests in and on animals and plants.

9 Claims, No Drawings

ARYLOXYPHENYLTHIOUREAS, ARYLOXYPHENYLISOTHIOUREAS AND ARYLOXYPHENYLCARBODIIMIDES AND PESTICIDAL COMPOSITIONS CONTAINING THEM

The present invention relates to novel substituted aryloxyphenyl-thioureas, -isothioureas and -carbodiimides, to their salts with organic and inorganic acids, to processes and intermediates for their preparation, to pesticidal compositions that contain these compounds, and to their use in the control of pests.

The compounds according to the invention correspond to formula I

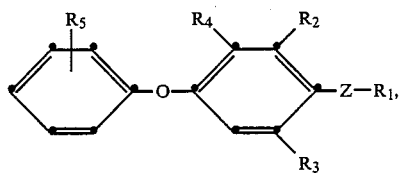

in which
$R_1$ represents $C_1$–$C_{12}$alkyl, $C_1$–$C_{12}$alkyl mono- or poly-substituted by halogen and/or by $C_1$–$C_6$alkoxy, $C_3$–$C_8$cycloalkyl, $C_3$–$C_8$cycloalkyl mono- or poly-substituted by $C_1$–$C_3$alkyl, or $C_3$–$C_8$cycloalkyl-$C_1$–$C_4$alkyl;
$R_2$ represents hydrogen or $C_1$–$C_5$alkyl;
$R_3$ represents $C_1$–$C_5$alkyl or $C_5$–$C_6$cycloalkyl;
$R_4$ represents hydrogen or methyl;
$R_5$ represents a $\text{-(CH=CH)}_2\text{-}$, $\text{-(CH}_2\text{)}_3\text{-}$ or $\text{-(CH}_2\text{)}_4\text{-}$ bridge in the 2,3- or 3,4-position;
Z represents —NH—CS—NH—, —N=C(SR$_6$)—NH— or —N=C=N— and
$R_6$ represents $C_1$–$C_{10}$alkyl or allyl.

Halogen atoms coming into consideration as substituents are fluorine and chlorine as well as bromine and iodine, fluorine and chlorine being preferred.

The alkyl radicals coming into consideration as substituents may be straight-chain or branched. Examples of such alkyl radicals that may be mentioned are methyl, ethyl, propyl, isopropyl, butyl, isobutyl, secbutyl, tert-butyl or pentyl, hexyl, octyl etc. and the isomers thereof.

The $C_1$–$C_{12}$alkyl radicals mono- or poly-substituted by halogen and/or by $C_1$–$C_6$alkoxy that come into consideration as substituents may be straight-chain or branched and may be only partially halogenated or perhalogenated and/or substituted from one to five times by $C_1$–$C_6$alkoxy, the above definitions applying to the halogen atoms and alkyl radicals. Suitable examples of such substituents are inter alia methyl mono- to tri-substituted by fluorine, chlorine and/or by bromine, such as, for example, $CHF_2$ or $CF_3$; ethyl substituted from one to five times by fluorine, chlorine and/or by bromine, such as, for example, $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or by bromine, such as, for example, $CH_2CHBrCH_2Br$, $CF_2CHFCF_3$, $CH_2CF_2CF_3$ or $CH(CF_3)_2$; butyl, or one of the isomers thereof, substituted from one to nine times by fluorine, chlorine and/or by bromine, such as, for example, $CF(CF_3)CHFCF_3$ or $CH_2(CF_2)_2CF_3$; methoxymethyl, methoxyethyl, ethoxyethyl, methoxypropyl, ethoxypropyl, propoxypropyl, methoxybutyl, ethoxybutyl, propoxybutyl or butoxybutyl, 1,2-dimethoxyethyl, 1,3-dimethoxypropyl or 2,4-dimethoxybutyl.

Cycloalkyl radicals coming into consideration as substituents are, for example, cyclopropyl, cyclobutyl, cyclopentyl or cyclohexyl. These radicals may be mono- or poly-substituted by a $C_1$–$C_3$alkyl radical and/or bonded via a $C_1$–$C_4$alkylene bridge to the rest of the molecule.

The compounds of formula I in which Z represents —N=C(SR$_6$)—NH— can also be in the form of acid addition salts. Both organic and inorganic acids are suitable for the formation of such salts. Examples of such acids are inter alia hydrochloric acid, hydrobromic acid, hydriodic acid, nitric acid, various phosphoric acids, sulfuric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid, phenylsulphonic acids or salicylic acid.

Compounds of formula I in which Z represents —N=C(SR$_6$)—NH— can be in the tautomeric forms

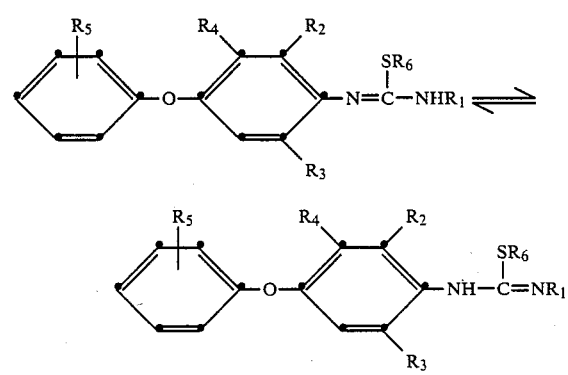

The invention includes both the individual tautomers and tautomeric mixtures.

Compounds of formula I that are of particular importance are those in which $R_1$ represents $C_1$–$C_8$alkyl, $C_1$–$C_8$alkyl mono- or poly-substituted by halogen and/or by $C_1$–$C_5$alkoxy, or $C_3$–$C_8$cycloalkyl, $R_2$ represents $C_1$–$C_5$-alkyl; $R_3$ represents $C_1$–$C_5$alkyl or cyclopentyl; $R_4$ represents hydrogen; $R_5$ represents a $\text{-(CH=CH)}_2\text{-}$, $\text{-(CH}_2\text{)}_3\text{-}$ or $\text{-(CH}_2\text{)}_4\text{-}$ bridge in the 2,3- or 3,4-position; Z represents —NH—CS—NH—, —N=C(SR$_6$)—NH— or —N=C=N—; and $R_6$ represents $C_1$–$C_5$alkyl or allyl.

Preferred compounds of formula I are those in which (a) $R_1$ represents $C_1$–$C_4$alkyl; $R_2$ and $R_3$ each represents $C_1$–$C_3$alkyl; $R_4$ represents hydrogen; $R_5$ represents a $\text{-(CH=CH)}_2\text{-}$ or $\text{-(CH}_2\text{)}_3\text{-}$ bridge in the 3,4-position; and Z represents —NH—CS—NH—, or (b) $R_1$ represents $C_1$–$C_4$alkyl; $R_2$ and $R_3$ each represents $C_1$–$C_3$alkyl; $R_4$ represents hydrogen; $R_5$ represents a $\text{-(CH=CH)}_2\text{-}$ or $\text{-(CH}_2\text{)}_3\text{-}$ bridge in the 3,4-position; Z represents —N=C(SR$_6$)—NH—; and $R_6$ represents $C_1$–$C_3$-alkyl, or (c) $R_1$ represents $C_1$–$C_4$alkyl; $R_2$ and $R_3$ each represents $C_1$–$C_3$alkyl; $R_4$ represents hydrogen; $R_5$ represents a $\text{-(CH=CH)}_2\text{-}$ or $\text{-(CH}_2\text{)}_3\text{-}$ bridge in the 3,4-position; and Z represents —N=C=N—.

Examples of compounds of formula I are inter alia:

| R₁ | R₂ | R₃ | R₄ | R₅ | Z | R₆ |
|---|---|---|---|---|---|---|
| CH₃ | CH(CH₃)₂ | CH(CH₃)₂ | H | 3,4-(CH=CH)₂- | —NH—CS—NH— | |
| CH(CH₃)₂ | CH₃ | CH₃ | CH₃ | 3,4-(CH=CH)₂- | —NH—CS—NH— | |
| CH(CH₃)₂ | C₂H₅ | CH₂CH(CH₃)₂ | H | 3,4-(CH=CH)₂- | —NH—CS—NH— | |
| CH(CH₃)₂ | CH₃ | C₂H₅ | H | 3,4-(CH=CH)₂- | —NH—CS—NH— | |
| CH(CH₃)₂ | CH₃ | CH₃ | H | 3,4-(CH=CH)₂- | —NH—CS—NH— | |
| CH₂CH(CH₃)₂ | CH(CH₃)₂ | CH(CH₃)₂ | H | 3,4-(CH=CH)₂- | —NH—CS—NH— | |
| C(CH₃)₃ | CH₃ | CH₃ | CH₃ | 3,4-(CH=CH)₂- | —NH—CS—NH— | |
| C(CH₃)₃ | C₂H₅ | CH₂CH(CH₃)₂ | H | 3,4-(CH=CH)₂- | —NH—CS—NH— | |
| C(CH₃)₃ | CH₃ | C₂H₅ | H | 3,4-(CH=CH)₂- | —NH—CS—NH— | |
| C(CH₃)₃ | CH₃ | CH₃ | H | 3,4-(CH=CH)₂- | —NH—CS—NH— | |
| C(CH₃)₃ | CH₃ | C(CH₃)₃ | H | 3,4-(CH=CH)₂- | —NH—CS—NH— | |
| (CH₂)₃OC₄H₉ | CH(CH₃)₂ | Cyclopentyl | H | 3,4-(CH=CH)₂- | —NH—CS—NH— | |
| C(CH₃)₃-Cyclohexyl | CH(CH₃)₂ | Cyclohexyl | H | 3,4-(CH=CH)₂- | —NH—CS—NH— | |
| Cyclopropyl | CH(CH₃)₂ | CH(CH₃)₂ | H | 3,4-(CH=CH)₂- | —NH—CS—NH— | |
| Cyclopentyl | CH(CH₃)₂ | CH₂CH(CH₃)₂ | H | 3,4-(CH=CH)₂- | —NH—CS—NH— | |
| Cyclohexyl | C₂H₅ | C₂H₅ | H | 3,4-(CH=CH)₂- | —NH—CS—NH— | |
| 2,6-Dimethylcyclohexyl | CH(CH₃)₂ | CH(CH₃)₂ | H | 3,4-(CH=CH)₂- | —NH—CS—NH— | |
| Cyclooctyl | CH(CH₃)₂ | CH(CH₃)₂ | H | 3,4-(CH=CH)₂- | —NH—CS—NH— | |
| CH(CH₃)₂ | CH(CH₃)₂ | CH(CH₃)₂ | H | 2,3-(CH=CH)₂- | —NH—CS—NH— | |
| CH(CH₃)₂ | CH(CH₃)₂ | CH(CH₃)₂ | H | 2,3-(CH=CH)₂- | —NH—CS—NH— | |
| C(CH₃)₃ | C₂H₅ | C₂H₅ | H | 2,3-(CH=CH)₂- | —NH—CS—NH— | |
| C(CH₃)₃ | CH(CH₃)₂ | CH(CH₃)₂ | H | 3,4-(CH₂)₂- | —NH—CS—NH— | |
| C(CH₃)₃ | C₂H₅ | C₂H₅ | H | 3,4-(CH₂)₂- | —NH—CS—NH— | |
| C(CH₃)₃ | CH₃ | CH₃ | H | 3,4-(CH₂)₂- | —NH—CS—NH— | |
| C(CH₃)₃ | CH(CH₃)₂ | CH(CH₃)₂ | H | 2,3-(CH₂)₂- | —NH—CS—NH— | |
| C(CH₃)₃ | C₂H₅ | C₂H₅ | H | 2,3-(CH₂)₂- | —NH—CS—NH— | |
| C(CH₃)₃ | CH₃ | CH₃ | H | 2,3-(CH₂)₂- | —NH—CS—NH— | |
| CH₃ | CH(CH₃)₂ | CH(CH₃)₂ | H | 3,4-(CH=CH)₂- | —N=C(SR₆)—NH— | CH₃ |
| C₂H₅ | CH(CH₃)₂ | CH(CH₃)₂ | CH₃ | 3,4-(CH=CH)₂- | —N=C(SR₆)—NH— | CH₃ |
| CH(CH₃)₂ | CH₃ | CH₃ | CH₃ | 3,4-(CH=CH)₂- | —N=C(SR₆)—NH— | CH₃ |
| CH(CH₃)₂ | C₂H₅ | CH₂CH(CH₃)₂ | H | 3,4-(CH=CH)₂- | —N=C(SR₆)—NH— | CH₃ |
| CH(CH₃)₂ | CH₃ | C₂H₅ | H | 3,4-(CH=CH)₂- | —N=C(SR₆)—NH— | CH₃ |
| CH(CH₃)₂ | CH₃ | CH₃ | H | 3,4-(CH=CH)₂- | —N=C(SR₆)—NH— | CH₃ |
| CH₂CH(CH₃)₂ | CH(CH₃)₂ | CH(CH₃)₂ | H | 3,4-(CH=CH)₂- | —N=C(SR₆)—NH— | CH₃ |
| C(CH₃)₃ | CH₃ | CH₃ | CH₃ | 3,4-(CH=CH)₂- | —N=C(SR₆)—NH— | CH₃ |
| C(CH₃)₃ | C₂H₅ | C₂H₅ | H | 3,4-(CH=CH)₂- | —N=C(SR₆)—NH— | CH₃ |
| C(CH₃)₃ | CH₃ | CH₃ | H | 3,4-(CH=CH)₂- | —N=C(SR₆)—NH— | CH₃ |
| C(CH₃)₃ | CH₃ | C(CH₃)₃ | H | 3,4-(CH=CH)₂- | —N=C(SR₆)—NH— | CH₃ |
| CH(CH₃)₃ | CH(CH₃)₂ | Cyclopentyl | H | 3,4-(CH=CH)₂- | —N=C(SR₆)—NH— | CH₃ |
| C(CH₃)₃ | CH(CH₃)₂ | Cyclohexyl | H | 3,4-(CH=CH)₂- | —N=C(SR₆)—NH— | CH₃ |
| CH[CH(CH₃)₂]₂ | CH(CH₃)₂ | CH(CH₃)₂ | H | 3,4-(CH=CH)₂- | —N=C(SR₆)—NH— | CH₃ |
| C₁₂H₂₅ | CH(CH₃)₂ | CH(CH₃)₂ | H | 3,4-(CH=CH)₂- | —N=C(SR₆)—NH— | CH₃ |
| (CH₂)₃OC₄H₉ | CH(CH₃)₂ | CH(CH₃)₂ | H | 3,4-(CH=CH)₂- | —N=C(SR₆)—NH— | CH₃ |
| C(CH₃)₂CF₃ | CH(CH₃)₂ | CH(CH₃)₂ | H | 3,4-(CH=CH)₂- | —N=C(SR₆)—NH— | CH₃ |
| C(CH₃)₂—Cyclohexyl | CH(CH₃)₂ | CH(CH₃)₂ | H | 3,4-(CH=CH)₂- | —N=C(SR₆)—NH— | CH₃ |

-continued

| R₁ | R₂ | R₃ | R₄ | R₅ | Z | R₆ |
|---|---|---|---|---|---|---|
| Cyclopentyl | CH(CH₃)₂ | CH(CH₃)₂ | H | 3,4-(CH=CH)₂- | —N=C(SR₆)—NH— | CH₃ |
| Cyclopropyl | CH(CH₃)₂ | CH(CH₃)₂ | H | 3,4-(CH=CH)₂- | —N=C(SR₆)—NH— | CH₃ |
| Cyclopentyl | C₂H₅ | CH₂CH(CH₃)₂ | H | 3,4-(CH=CH)₂- | —N=C(SR₆)—NH— | CH₃ |
| Cyclohexyl | CH(CH₃)₂ | CH(CH₃)₂ | H | 3,4-(CH=CH)₂- | —N=C(SR₆)—NH— | CH₃ |
| 2,6-Dimethylcyclohexyl | CH(CH₃)₂ | CH(CH₃)₂ | H | 3,4-(CH=CH)₂- | —N=C(SR₆)—NH— | CH₃ |
| Cyclooctyl | CH(CH₃)₂ | CH(CH₃)₂ | H | 3,4-(CH=CH)₂- | —N=C(SR₆)—NH— | CH₃ |
| CH(CH₃)₂ | CH(CH₃)₂ | CH(CH₃)₂ | H | 3,4-(CH=CH)₂- | —N=C(SR₆)—NH— | CH₃ |
| CH(CH₃)₂ | C₂H₅ | C₂H₅ | H | 2,3-(CH=CH)₂- | —N=C(SR₆)—NH— | CH₃ |
| C(CH₃)₃ | C(CH₃)₃ | CH(CH₃)₂ | H | 2,3-(CH=CH)₂- | —N=C(SR₆)—NH— | CH₃ |
| C(CH₃)₃ | C₂H₅ | CH(CH₃)₂ | H | 3,4-(CH=CH)₂- | —N=C(SR₆)—NH— | CH₃ |
| CH(CH₃)₂ | CH(CH₃)₂ | CH(CH₃)₂ | H | 3,4-(CH₂)₂- | —N=C(SR₆)—NH— | CH₃ |
| C(CH₃)₃ | CH₂CH(CH₃)₂ | CH₂CH(CH₃)₂ | H | 2,3-(CH₂)₂- | —N=C(SR₆)—NH— | CH₃ |
| C(CH₃)₃ | C₂H₅ | C₂H₅ | H | 3,4-(CH₂)₂- | —N=C(SR₆)—NH— | CH₃ |
| C(CH₃)₃ | CH₃ | CH₃ | H | 2,3-(CH₂)₂- | —N=C(SR₆)—NH— | CH₃ |
| CH(CH₃)₂ | CH(CH₃)₂ | CH(CH₃)₂ | H | 3,4-(CH₂)₂- | —N=C(SR₆)—NH— | CH₃ |
| CH(CH₃)₂ | CH(CH₃)₂ | C₂H₅ | H | 2,3-(CH₂)₂- | —N=C(SR₆)—NH— | CH₃ |
| C(CH₃)₃ | CH(CH₃)₂ | CH(CH₃)₂ | H | 3,4-(CH₂)₂- | —N=C(SR₆)—NH— | CH₃ |
| C(CH₃)₃ | C₂H₅ | C₂H₅ | H | 2,3-(CH₂)₂- | —N=C(SR₆)—NH— | CH₃ |
| CH(CH₃)₂ | CH(CH₃)₂ | CH(CH₃)₂ | H | 3,4-(CH=CH)₂- | —N=C(SR₆)—NH— | C₂H₅ |
| CH(CH₃)₂ | CH(CH₃)₂ | CH(CH₃)₂ | H | 3,4-(CH=CH)₂- | —N=C(SR₆)—NH— | C₃H₇ |
| C(CH₃)₃ | CH(CH₃)₂ | CH(CH₃)₂ | H | 3,4-(CH=CH)₂- | —N=C(SR₆)—NH— | C₆H₁₃ |
| C(CH₃)₃ | CH(CH₃)₂ | CH(CH₃)₂ | H | 3,4-(CH=CH)₂- | —N=C(SR₆)—NH— | C₁₀H₂₁ |
| C(CH₃)₃ | CH(CH₃)₂ | CH(CH₃)₂ | H | 3,4-(CH=CH)₂- | —N=C(SR₆)—NH— | CH₂—CH=CH₂ |
| CH₃ | CH₃ | CH₃ | CH₃ | 3,4-(CH=CH)₂- | —N=C=N— | |
| C₂H₅ | C₂H₅ | CH₂CH(CH₃)₂ | H | 3,4-(CH=CH)₂- | —N=C=N— | |
| CH(CH₃)₂ | CH(CH₃)₂ | CH₃ | H | 3,4-(CH=CH)₂- | —N=C=N— | |
| CH(CH₃)₂ | CH₃ | CH₂CH(CH₃)₂ | CH₃ | 3,4-(CH=CH)₂- | —N=C=N— | |
| CH(CH₃)₂ | CH₃ | CH₃ | H | 3,4-(CH=CH)₂- | —N=C=N— | |
| CH(CH₃)₂ | CH(CH₃)₂ | CH(CH₃)₂ | CH₃ | 3,4-(CH=CH)₂- | —N=C=N— | |
| CH₂CH(CH₃)₂ | CH(CH₃)₂ | CH(CH₃)₂ | H | 3,4-(CH=CH)₂- | —N=C=N— | |
| C(CH₃)₃ | CH₃ | CH₃ | H | 3,4-(CH=CH)₂- | —N=C=N— | |
| C(CH₃)₃ | CH(CH₃)₂ | C(CH₃)₃ | H | 3,4-(CH=CH)₂- | —N=C=N— | |
| C(CH₃)₃ | CH(CH₃)₂ | CH₂CH(CH₃)₂ | H | 3,4-(CH=CH)₂- | —N=C=N— | |
| C(CH₃)₃ | CH(CH₃)₂ | Cyclopentyl | H | 3,4-(CH=CH)₂- | —N=C=N— | |
| (CH₂)₃OC₄H₉ | CH(CH₃)₂ | Cyclohexyl | H | 3,4-(CH=CH)₂- | —N=C=N— | |
| C(CH₃)₃ | CH(CH₃)₂ | CH(CH₃)₂ | H | 3,4-(CH=CH)₂- | —N=C=N— | |
| Cyclopropyl | CH(CH₃)₂ | CH₂CH(CH₃)₂ | H | 3,4-(CH=CH)₂- | —N=C=N— | |
| Cyclopentyl | CH(CH₃)₂ | CH(CH₃)₂ | H | 3,4-(CH=CH)₂- | —N=C=N— | |
| 2,6-Dimethylcyclohexyl | C₂H₅ | CH(CH₃)₂ | H | 3,4-(CH=CH)₂- | —N=C=N— | |
| Cyclooctyl | CH(CH₃)₂ | CH(CH₃)₂ | H | 3,4-(CH=CH)₂- | —N=C=N— | |
| CH(CH₃)₂ | CH(CH₃)₂ | CH(CH₃)₂ | H | 2,3-(CH=CH)₂- | —N=C=N— | |
| C(CH₃)₃ | CH(CH₃)₂ | CH(CH₃)₂ | H | 2,3-(CH=CH)₂- | —N=C=N— | |
| C(CH₃)₃ | C₂H₅ | C₂H₅ | H | 2,3-(CH=CH)₂- | —N=C=N— | |
| CH(CH₃)₂ | CH(CH₃)₂ | CH(CH₃)₂ | H | 3,4-(CH₂)₂- | —N=C=N— | |
| C(CH₃)₃ | CH(CH₃)₂ | CH₂CH(CH₃)₂ | H | 3,4-(CH₂)₂- | —N=C=N— | |

-continued

| R₁ | R₂ | R₃ | R₄ | R₅ | Z | R₆ |
|---|---|---|---|---|---|---|
| C(CH₃)₃ | CH₃ | C₂H₅ | H | 3,4-(CH₂)₃- | —N=C=N— | |
| C(CH₃)₃ | CH₃ | CH₃ | H | 3,4-(CH₂)₃- | —N=C=N— | |
| CH(CH₃)₂ | CH(CH₃)₂ | CH(CH₃)₂ | H | 2,3-(CH₂)₄- | —N=C=N— | |
| CH(CH₃)₂ | C₂H₅ | C₂H₅ | H | 2,3-(CH₂)₄- | —N=C=N— | |
| C(CH₃)₃ | CH(CH₃)₂ | CH(CH₃)₂ | H | 2,3-(CH₂)₄- | —N=C=N— | |
| C(CH₃)₃ | C₂H₅ | C₂H₅ | H | 2,3-(CH₂)₄- | —N=C=N— | |

The compounds of formula I according to the invention can be prepared according to processes that are known in principle, for example as follows:

(A) an isothiocyanate of formula II

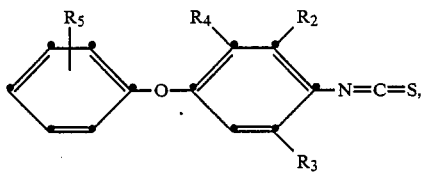

is reacted with an amine of formula III $$H_2N—R_1 \quad (III)$$

to form thiourea and optionally (B) the resulting thiourea is reacted with a compound of formula IV $$X—R_6 \quad (IV)$$

to form isothiourea, or (C) the resulting thiourea is converted into the carbodiimide by removal of hydrogen sulphide. $R_1$, $R_2$, $R_3$, $R_4$, $R_5$ and $R_6$ have the meanings given and X represents a suitable leaving group, such as, for example, a halogen atom, especially chlorine, bromine or iodine, or alkyl sulphate.

Process A is customarily carried out under normal pressure and in the presence of an organic solvent or diluent. The temperature is from 0° to +150° C., preferably from +10° to 70° C. As solvents and diluents there are suitable, for example, ethers and ethereal compounds, such as diethyl ether, dipropyl ether, dibutyl ether, dioxan, dimethoxyethane or tetrahydrofuran; N,N-dialkylated carboxylic acid amides; aliphatic, aromatic and halogenated hydrocarbons, such as benzene, toluene, xylenes, chloroform, methylene chloride, carbon tetrachloride, chlorobenzene; nitriles, such as acetonitrile or propionitrile; ketones, such as acetone, methyl ethyl ketone, methyl isopropyl ketone, methyl isobutyl ketone or cyclohexanone.

Process B is advantageously carried out in an inert organic solvent and under slightly elevated or normal pressure. The temperature is from +10° to 250° C., preferably the boiling temperature of the solvent used or from +50° to 150° C. Suitable solvents or diluents are, for example, ethers or ethereal compounds, such as diethyl ether, diisopropyl ether, dioxan or tetrahydrofuran; aromatic hydrocarbons, such as benzene, toluene or xylenes; ketones, such as acetone, methyl ethyl ketone or cyclohexanone, alcohols or dimethylformamide.

Process C is advantageously carried out in an aprotic organic solvent or diluent under normal pressure. The temperature is from 0° to +150° C., preferably from +10° to 50° C. Suitable solvents or diluents are, for example, ethers or ethereal compounds, such as diethyl ether, dipropyl ether, dibutyl ether, dioxan, dimethoxyethane or tetrahydrofuran; N,N-dialkylated carboxylic acid amides; aliphatic, aromatic and halogenated hydrocarbons, such as benzene, toluene, xylenes, chloroform, methylene chloride, carbon tetrachloride or chlorobenzene; nitriles, such as acetonitrile or propionitrile; ketones, such as acetone, methyl ethyl ketone, methyl isopropyl ketone or cyclohexanone. The removal of hydrogen sulphide is effected according to procedures described in the literature (T. Shibanuma, Chemistry Letters 1977, p. 575–576; S. Kim, Tetrahedron Letters 1985, p. 1661–1664; W. Weith, Vol. 6, 1873, p. 1398; G. Amiard, Bull. Soc. chim. 1956, p. 1360). As removal reagents there are used inter alia HgO, certain pyridinium salts, chloroacetic acid esters, cyanuric acid chloride, p-toluenesulfochloride or certain phosphoric acid ester derivatives.

The isothiocyanates of formula II can be prepared according to methods known in principle, for example by reacting a phenoxyaniline of formula V

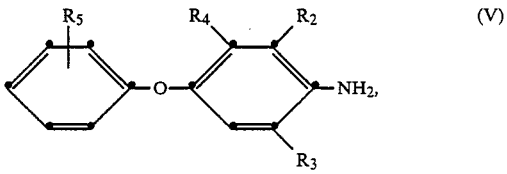

with thiophosgene, $R_2$, $R_3$, $R_4$ and $R_5$ having the meanings given for formula I.

The process for the preparation of the compounds of formula II is advantageously carried out under normal pressure in the presence of an organic or inorganic base, such as, for example, triethylamine or calcium carbonate, and a solvent or diluent that is inert towards the reactants. The temperature is from 0° to +100° C., preferably the boiling temperature of the solvent or diluent used or from +20° to 80° C. Suitable solvents and diluents are inter alia ethers or ethereal compounds, such as, for example, diethyl ether, diisopropyl ether, dioxan or tetrahydrofuran; aromatic hydrocarbons, such as benzene, toluene or xylenes; ketones, such as acetone, methyl ethyl ketone or cyclohexanone; or chlorinated hydrocarbons, such as, for example, dichloromethane. The preparation may also take place in the presence of water in a two-phase system.

The phenoxyanilines of formula V can be prepared according to methods known in principle, for example by reacting an aniline of formula VI

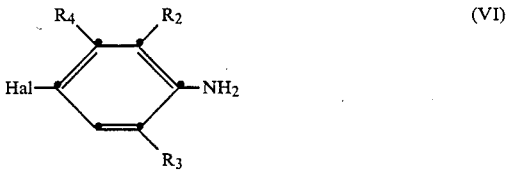

with a phenol of formula VII

$R_2$, $R_3$, $R_4$ and $R_5$ having the meanings given for formula I and Hal representing halogen, especially chlorine or bromine.

The process for the preparation of compounds of formula V is advantageously carried out under normal pressure in the presence of an organic or, especially, an inorganic base, such as, for example, an alkali metal hydroxide or carbonate, and a solvent or diluent, preferably a polar solvent or diluent, that is inert towards the reactants. The temperature is from 0° to +200° C., preferably the boiling temperature of the solvent or diluent used or from +50° to 170° C. The addition of a heavy metal catalyst, such as, for example, copper powder or basic copper(II) carbonate may also prove advantageous. Suitable solvents and diluents are inter alia amides, such as dimethylformamide, dimethyl sulphoxide, N-methyl pyrrolidone and other polar aprotic solvents.

The compounds of formulae II and V are novel and the present invention relates also to these. The compounds of formulae III, IV, VI and VII are, however, known or can be prepared according to methods known in principle.

Surprisingly it has been found that the compounds of formula I according to the invention are valuable active ingredients in the control of pests while being well tolerated by warm-blooded animals and by plants. The compounds of formula I are therefore suitable, for example, for controlling pests in and on animals and plants. Such pests belong chiefly to the family of arthropods, such as, especially, insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera, and arachnids of the order Acarina, such as, for example, mites and ticks. It is possible to control each stage of development of the pests, that is to say the adults, pupae and nymphs as well as, especially, the larvae and eggs. Above all it is possible to control effectively the larvae and eggs of phytopathogenic insect and mite pests in ornamentals and useful plants, such as in fruit and vegetables, and especially in cotton. If the compounds of formula I are ingested by imagines, their action can manifest itself in the immediate death of the pests or in reduced oviposition and/or hatching rates. The latter phenomenon is to be observed especially in Coleoptera. In the control of pests that parasiticise animals, especially domestic animals and productive livestock, there come into consideration especially ectoparasites, such as, for example, mites and ticks, and Diptera, such as, for example, *Lucilia sericata*.

The good pesticidal action of the compounds of formula I according to the invention corresponds to a mortality of at least 50–60% of the mentioned pests.

The action of the compounds of the invention or the compositions containing them can be considerably broadened and adapted to the prevailing circumstances by the addition of other insecticides and/or acaricides. Additives that come into consideration are, for example, representatives of the following classes of active ingredients: organic phosphorus compounds, nitrophenols and derivatives, formamidines, ureas, carbamates, pyrethroids, chlorinated hydrocarbons and *Bacillus thuringiensis* preparations.

The compounds of formula I are used in unmodified form, or preferably together with the inert adjuvants, tolerated by plants, that are conventionally employed in the art of formulation, and can therefore be formulated in known manner, for example, to emulsifiable concentrates, directly sprayable or dilutable solutions, dilute emulsions, wettable powders, soluble powders, dusts, granulates, and also encapsulations in, for example, polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing the active ingredient of formula I or combinations thereof with other insecticides or acaricides, and, where appropriate, a solid or liquid adjuvant, are prepared in known manner, for example by homogeneously mixing and/or grinding the active ingredients with extenders, for example solvents, solid carriers and, in some cases, surface-active compounds (surfactants).

Suitable solvents are: aromatic hydrocarbons, preferably the fractions containing 8 to 12 carbon atoms, for example xylene mixtures or substituted naphthalenes, phthalates such as dibutyl phthalate or dioctyl phthalate, aliphatic hydrocarbons such as cyclohexane, paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, as well as vegetable oils or epoxidised vegetable oils such as epoxidised coconut oil or soybean oil; or water.

The solid carriers used, for example for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolate or bentonite; and suitable nonsorbent carriers are materials such as calcite or sand. In addition a great number of granulated materials of inorganic or organic nature can be used, for example especially dolomite or pulverised plant residues.

Depending upon the nature of the active ingredient of formula I or combinations of these active ingredients with other insecticides or acaricides to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both so-called water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), for example the sodium or potassium salts of oleic or stearic acid, or of natural fatty acid mixtures which can be obtained, for example, from coconut oil or tall oil. Further suitable surfactants are also the fatty acid methyl taurin salts, and modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, for example the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms.

Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, for example salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, for example polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, for example stearyltrimethylammonium chloride or benzyldi(2-chloroethyl)ethylammonium bromide.

The surfactants customarily employed in the art of formulation are described, inter alia, in the following publications:

"McCutcheon's Detergents and Emulsifiers Annual", MC Publishing Corp., Ridgewood, N.J., 1979; Dr. Helmut Stache, "Tensid-Taschenbuch" (Handbook of Surfactants), Carl Hanser Verlag, Munich/Vienna 1981.

The pesticidal compositions usually contain 0.1 to 99%, preferably 0.1 to 95%, of active ingredient of formula I or combinations of these active ingredients with other insecticides or acaricides, 1 to 99.9% of a solid or liquid adjuvant, and 0 to 25%, preferably 0.1 to 20%, of a surfactant. Whereas commercial products are preferably formulated as concentrates, the end user will normally employ diluted formulations containing considerably lower concentrations of active ingredient.

The compositions may also contain further ingredients, such as stabilisers, antifoams, viscosity regulators, binders and tackifiers, as well as fertilisers or other active ingredients in order to obtain special effects.

EXAMPLE 1

Preparation 1.1. Intermediates
1.1.1. 4-aryloxyanilines
1.1.1.1. 2,6-diisopropyl-4-(naphthyl-2-oxy)-aniline 120 g of 2-naphthol are dissolved in 800 ml of xylene and, under nitrogen, 55 g of pulverised potassium hydroxide are added thereto. The reaction mixture is heated to boiling with stirring and the water is removed. After the addition of 5 g of copper chloride and 160 g of 2,6-diisopropyl-4-bromoaniline, the mixture is stirred for 12 hours at 150°–155° C., then cooled, and the resulting precipitate is filtered off with suction. The filtrate is washed with a 15% aqueous solution of sodium hydroxide and twice with 200 ml of water each time. The organic phase is separated off, dried over sodium sulfate and freed of solvent, and the residue is distilled. The title compound of formula

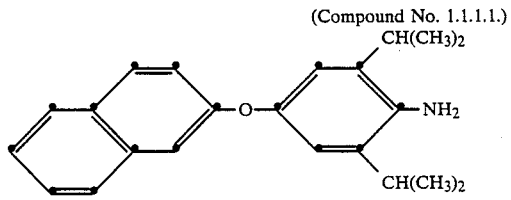

(Compound No. 1.1.1.1.)

is obtained in the form of a light-yellow liquid; b.p. 173° C./0.06 torr.

The following compounds are prepared in an analogous manner:

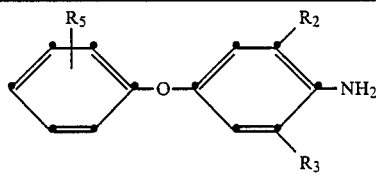

| Comp. No. | $R_2$ | $R_3$ | $R_5$ | phys. data |
|---|---|---|---|---|
| 1.1.1.2. | $C_2H_5$ | $C_2H_5$ | 3,4-(CH=CH-)$_2$ | m.p. 58–61° C. |
| 1.1.1.3. | $C_2H_5$ | $C_2H_5$ | 3,4-(CH$_2$-)$_3$ | B.p. 173–175° C./0.03 Torr |
| 1.1.1.4. | $C_2H_5$ | Cyclopentyl | 3,4-(CH=CH-)$_2$ | m/e = 331 |

1.1.2. Aryloxyphenylisothiocyanates 1.1.2.1. 2,6-diisopropyl-4-(naphthyl-2-oxy)-phenylisothiocyanate 50.0 g of 2,6-diisopropyl-4-(naphthyl-2-oxy)-aniline dissolved in 100 ml of dichloromethane are added dropwise at from 0° to +10° C., with vigorous stirring, to 21.6 g of thiophosgene, 300 ml of dichloromethane, 200 ml of water and 31.3 g of ground calcium carbonate. The reaction mixture is stirred for 2 hours at room temperature and then filtered. The organic phase is separated off, washed with 200 ml of water, dried over sodium sulfate and then concentrated by evaporation. The title compound of formula

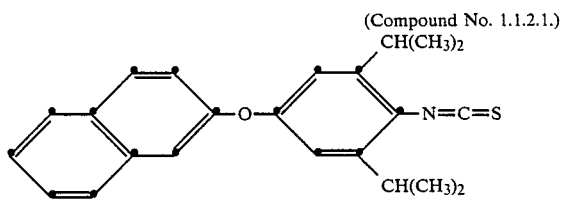

(Compound No. 1.1.2.1.)

is obtained as a crude product in the form of a yellow oil and can be processed further in this state. On leaving to stand crystals are formed; m.p. 76°–78° C.

The following compounds are prepared in an analogous manner:

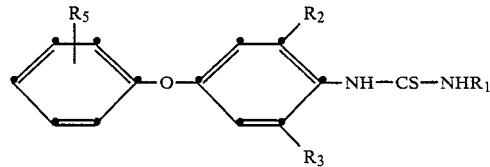

| Comp. No. | $R_1$ | $R_2$ | $R_3$ | $R_5$ | M.p. °C. |
|---|---|---|---|---|---|
| 1.2.1.2. | $CH(CH_3)_2$ | $CH(CH_3)_2$ | $CH(CH_3)_2$ | $3,4\text{-}(CH=CH)_2$ | 173–175 |
| 1.2.1.3. | $C(CH_3)_3$ | $C_2H_5$ | $C_2H_5$ | $3,4\text{-}(CH=CH)_2$ | 108–110 |
| 1.2.1.4. | $CH(CH_3)_2$ | $C_2H_5$ | $C_2H_5$ | $3,4\text{-}(CH=CH)_2$ | 143–145 |
| 1.2.1.5. | $C(CH_3)_3$ | $C_2H_5$ | $C_2H_5$ | $3,4\text{-}(CH_2)_3$ | 100–102 |
| 1.2.1.6. | $CH(CH_3)_2$ | $C_2H_5$ | $C_2H_5$ | $3,4\text{-}(CH_2)_3$ | 148–150 |
| 1.2.1.7. | $CH_2CF_3$ | $CH(CH_3)_2$ | $CH(CH_3)_2$ | $3,4\text{-}(CH=CH)_2$ | 107–109 |
| 1.2.1.8. | $CH[CH(CH_3)_2]_2$ | $CH(CH_3)_2$ | $CH(CH_3)_2$ | $3,4\text{-}(CH=CH)_2$ | 154–155 |
| 1.2.1.9. | $C_{12}H_{25}$ | $CH(CH_3)_2$ | $CH(CH_3)_2$ | $3,4\text{-}(CH=CH)_2$ | 79–81 |
| 1.2.1.10. | $C(CH_3)_2C_2H_5$ | $CH(CH_3)_2$ | $CH(CH_3)_2$ | $3,4\text{-}(CH=CH)_2$ | 150/decomp. |
| 1.2.1.11. | Cyclopentyl | $CH(CH_3)_2$ | $CH(CH_3)_2$ | $3,4\text{-}(CH=CH)_2$ | 191–194 |
| 1.2.1.12. | $C_2H_5$ | $CH(CH_3)_2$ | $CH(CH_3)_2$ | $3,4\text{-}(CH=CH)_2$ | 172–175 |
| 1.2.1.13. | $CH(CH_3)C_2H_5$ | $CH(CH_3)_2$ | $CH(CH_3)_2$ | $3,4\text{-}(CH=CH)_2$ | 156–158 |
| 1.2.1.14. | $CH(CH_3)_2$ | $C_2H_5$ | Cyclopentyl | $3,4\text{-}(CH=CH)_2$ | 137.5–138 |
| 1.2.1.15. | $C(CH_3)_3$ | $C_2H_5$ | Cyclopentyl | $3,4\text{-}(CH=CH)_2$ | 72–74 |

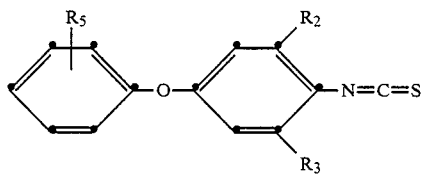

| Comp. No. | $R_2$ | $R_3$ | $R_5$ | phys. data |
|---|---|---|---|---|
| 1.1.2.2. | $C_2H_5$ | $C_2H_5$ | $3,4\text{-}(CH=CH)_2$ | m.p. 55–58° C. |
| 1.1.2.3. | $C_2H_5$ | $C_2H_5$ | $3,4\text{-}(CH_2)_3$ | m.p. 48–50° C. |
| 1.1.2.4. | $C_2H_5$ | Cyclopentyl | $3,4\text{-}(CH=CH)_2$ | $n_D^{24}$: 1.6660 |

1.2. End products 1.2.1. Aryloxyphenylthioureas 1.2.1.1. N-[2,6-diisopropyl-4-(naphthyl-2-oxy)-phenyl]-N'-tert-butylthiourea 25.0 g of 2,6-diisopropyl-4-(naphthyl-2-oxy)-phenylisothiocyanate are dissolved in 100 ml of hexane and, with stirring, 7.7 g of tert-butylamine are added thereto. The reaction mixture is stirred at 20° to 25° C. for 12 hours. The resulting precipitate is then filtered off with suction, washed with hexane and dried. The title compound of the formula

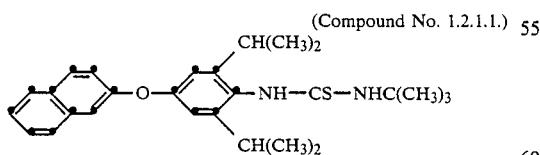

(Compound No. 1.2.1.1.)

is obtained in the form of a light-beige powder; m.p. 155° C. (decomposition).

The following compounds are prepared in an analogous manner:

1.2.2. Aryloxyphenylisothioureas 1.2.2.1. N-[2,6-diisopropyl-4-(naphthyl-2-oxy)-phenyl]-N'-tert-butyl-S-methylisothiourea 2.7 g of methyl iodide are added at room temperature to 5.0 g of N-[2,6-diisopropyl-4-(naphthyl-2-oxy)-phenyl]-N'-tert-butylthiourea in 40 ml of ethanol and the mixture is stirred for 6 hours under gentle reflux. The solvent is then evaporated off and the residue is taken up in 80 ml of dichloromethane and 40 ml of 10% aqueous soda solution. The organic phase is separated off, dried over sodium sulfate and freed of solvent. The residue is stirred in hexane, filtered off and dried. The title compound of formula

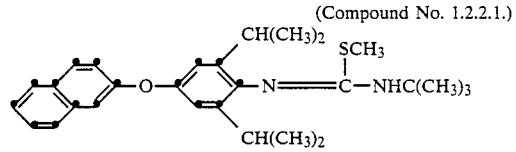

(Compound No. 1.2.2.1.)

is obtained in the form of a light-beige powder; m.p. 102°–102° C.

The following compounds are prepared in an analogous manner:

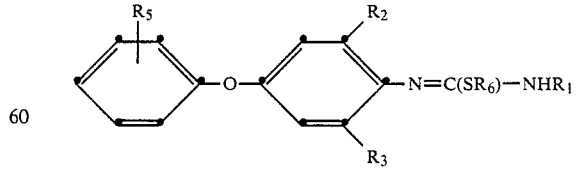

| Comp. No. | $R_1$ | $R_2$ | $R_3$ | $R_5$ | $R_6$ | phys. data |
|---|---|---|---|---|---|---|
| 1.2.2.2. | $CH(CH_3)_2$ | $CH(CH_3)_2$ | $CH(CH_3)_2$ | $3,4\text{-}(CH=CH)_2$ | $CH_3$ | Harz |
| 1.2.2.3. | $C(CH_3)_3$ | $C_2H_5$ | $C_2H_5$ | $3,4\text{-}(CH=CH)_2$ | $CH_3$ | m.p. 96–97° C. |
| 1.2.2.4. | $CH(CH_3)_2$ | $C_2H_5$ | $C_2H_5$ | $3,4\text{-}(CH=CH)_2$ | $CH_3$ | $n_D^{22}$: 1.6174 |

-continued

| Comp. No. | R1 | R2 | R3 | R5 | R6 | phys. data |
|---|---|---|---|---|---|---|
| 1.2.2.5. | $C(CH_3)_3$ | $CH(CH_3)_2$ | $CH(CH_3)_2$ | 3,4-$(CH=CH)_2$ | $C_2H_5$ | m.p. 117–120° C. |
| 1.2.2.6. | $C(CH_3)_3$ | $CH(CH_3)_2$ | $CH(CH_3)_2$ | 3,4-$(CH=CH)_2$ | $C_3H_7$ | m.p. 100–102° C. |
| 1.2.2.7. | $C(CH_3)_3$ | $CH(CH_3)_2$ | $CH(CH_3)_2$ | 3,4-$(CH=CH)_2$ | $C_4H_9$ | m.p. 90–93° C. |
| 1.2.2.8. | $C(CH_3)_3$ | $CH(CH_3)_2$ | $CH(CH_3)_2$ | 3,4-$(CH=CH)_2$ | $C_6H_{13}$ | m.p. 60–64° C. |
| 1.2.2.9. | $C(CH_3)_3$ | $CH(CH_3)_2$ | $CH(CH_3)_2$ | 3,4-$(CH=CH)_2$ | $C_{10}H_{21}$ | m.p. 72–74° C. |
| 1.2.2.10. | $CH_2CF_3$ | $CH(CH_3)_2$ | $CH(CH_3)_2$ | 3,4-$(CH=CH)_2$ | $CH_3$ | $n_D^{24}$: 1.577 |
| 1.2.2.11. | $CH[CH(CH_3)_2]_2$ | $CH(CH_3)_2$ | $CH(CH_3)_2$ | 3,4-$(CH=CH)_2$ | $CH_3$ | $n_D^{24}$: 1.583 |
| 1.2.2.12. | $C_{12}H_{25}$ | $CH(CH_3)_2$ | $CH(CH_3)_2$ | 3,4-$(CH=CH)_2$ | $CH_3$ | $n_D^{24}$: 1.5662 |
| 1.2.2.13. | $C(CH_3)_2C_2H_5$ | $CH(CH_3)_2$ | $CH(CH_3)_2$ | 3,4-$(CH=CH)_2$ | $CH_3$ | m.p. 102–104° C. |
| 1.2.2.14. | Cyclopentyl | $CH(CH_3)_2$ | $CH(CH_3)_2$ | 3,4-$(CH=CH)_2$ | $CH_3$ | m.p. 97–99° C. |
| 1.2.2.15. | $C_2H_5$ | $CH(CH_3)_2$ | $CH(CH_3)_2$ | 3,4-$(CH=CH)_2$ | $CH_3$ | m.p. 75–78° C. |
| 1.2.2.16. | $CH(CH_3)C_2H_5$ | $CH(CH_3)_2$ | $CH(CH_3)_2$ | 3,4-$(CH=CH)_2$ | $CH_3$ | $n_D^{24}$: 1.596 |
| 1.2.2.17. | $CH(CH_3)_2$ | $C_2H_5$ | $C_2H_5$ | 3,4-$(CH=CH)_2$ | $C_2H_5$ | $n_D^{23}$: 1.610 |
| 1.2.2.18. | $CH(CH_3)_2$ | $C_2H_5$ | $C_2H_5$ | 3,4-$(CH=CH)_2$ | $C_3H_7$ | $n_D^{23}$: 1.600 |
| 1.2.2.19. | $C(CH_3)_3$ | $C_2H_5$ | $C_2H_5$ | 3,4-$(CH=CH)_2$ | $C_2H_5$ | $n_D^{23}$: 1.605 |
| 1.2.2.20. | $C(CH_3)_3$ | $C_2H_5$ | $C_2H_5$ | 3,4-$(CH=CH)_2$ | $C_3H_7$ | m.p. 76–78° C. |
| 1.2.2.21. | $C(CH_3)_3$ | $C_2H_5$ | $C_2H_5$ | 3,4-$(CH_2)_3$ | $CH_3$ | m.p. 103–105° C. |
| 1.2.2.22. | $C(CH_3)_3$ | $C_2H_5$ | $C_2H_5$ | 3,4-$(CH_2)_3$ | $C_2H_5$ | m.p. 84–86° C. |
| 1.2.2.23. | $C(CH_3)_3$ | $C_2H_5$ | $C_2H_5$ | 3,4-$(CH_2)_3$ | $C_3H_7$ | m.p. 86–87° C. |
| 1.2.2.24. | $CH(CH_3)_2$ | $C_2H_5$ | $C_2H_5$ | 3,4-$(CH_2)_3$ | $CH_3$ | $n_D^{20}$: 1.5758 |
| 1.2.2.25. | $CH(CH_3)_2$ | $C_2H_5$ | Cyclopentyl | 3,4-$(CH=CH)_2$ | $CH_3$ | $n_D^{24.5}$: 1.5989 |
| 1.2.2.26. | $C(CH_3)_3$ | $C_2H_5$ | Cyclopentyl | 3,4-$(CH=CH)_2$ | $CH_3$ | $n_D^{24}$: 1.59154 |

1.2.3.1. 4-toluenesulphonic acid salt of N-[2,6-diisopropyl-4-(naphthyl-2-oxy)-phenyl]-N'-tert-butyl-S-methylisothiourea 5.0 g of N-[2,6-diisopropyl-4-(naphthyl-2-oxy)-phenyl]-N'-tert-butyl-S-methylisothiourea are dissolved in 20 ml of absolute diethyl ether, and then 2.2 g of 4-toluenesulphonic acid dissolved in 10 ml of diethyl ether are added dropwise thereto. The reaction solution is stirred at room temperature for 3 hours. The resulting precipitate is filtered off with suction and dried. The title compound of formula

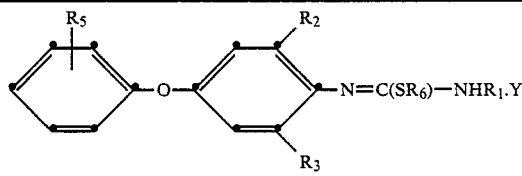

(Compound No. 1.2.3.1.)

is obtained in the form of a white crystalline powder; m.p. 180° C./decomposition.

The following compounds are prepared in an analogous manner:

| | $R_5$ | | $R_2$ | | | |
|---|---|---|---|---|---|---|

$$\text{structure: } -O- \text{ with } N=C(SR_6)-NHR_1 \cdot Y$$

| Comp. No. | R1 | R2 | R3 | R5 | R6 | Y | M.p. °C. |
|---|---|---|---|---|---|---|---|
| 1.2.3.2. | $C(CH_3)_3$ | $CH(CH_3)_2$ | $CH(CH_3)_2$ | 3,4-$(CH=CH)_2$ | $CH_3$ | HJ | 158/decomp. |

1.2.4. Aryloxyphenylcarbodiimides 1.2.4.1. N-[2,6-diisopropyl-4-(naphthyl-2-oxy)-phenyl]-N'-tert-butylcarbodiimide 2.5 g of triethylamine in 10 ml of acetonitrile are added dropwise at room temperature with stirring to 5.0 g of N-[2,6-diisopropyl-4-(naphthyl-2-oxy)-phenyl]-N'-tert-butylthiourea and 2.9 g of 2-chloro-1-methylpyridinium iodide in 40 ml of acetonitrile, and the mixture is stirred at 70° C. for 2 hours. The reaction mixture is then concentrated by evaporation in a rotary evaporator at 50° C. and the residue is taken up in 50 ml of hexane and 30 ml of cold water. The hexane phase is separated off, washed with 20 ml of cold water, dried over sodium sulfate and finally concentrated by evaporation. The title compound of formula

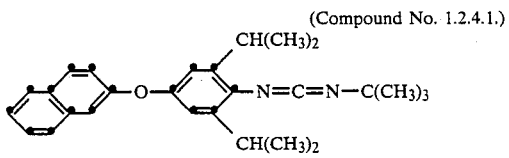

(Compound No. 1.2.4.1.)

is obtained in the form of a light-brown oil from which crystals are formed on leaving to stand; m.p. 48°–51° C.

The following compounds are prepared in an analogous manner:

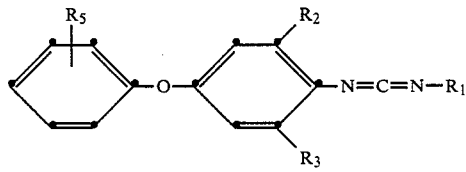

| Comp. No. | R$_1$ | R$_2$ | R$_3$ | R$_5$ | phys. data |
|---|---|---|---|---|---|
| 1.2.4.2. | CH(CH$_3$)$_2$ | CH(CH$_3$)$_2$ | CH(CH$_3$)$_2$ | 3,4—(CH=CH)$_2$— | n$_D^{40}$: 1.5942 |
| 1.2.4.3. | C(CH$_3$)$_3$ | C$_2$H$_5$ | C$_2$H$_5$ | 3,4—(CH=CH)$_2$— | n$_D^{24}$: 1.6070 |
| 1.2.4.4. | CH(CH$_3$)$_2$ | C$_2$H$_5$ | C$_2$H$_5$ | 3,4—(CH=CH)$_2$— | n$_D^{23}$: 1.6153 |
| 1.2.4.5. | C(CH$_3$)$_3$ | C$_2$H$_5$ | C$_2$H$_5$ | 3,4—(CH$_2$)$_3$— | n$_D^{20}$: 1.5743 |
| 1.2.4.6. | CH(CH$_3$)$_2$ | C$_2$H$_5$ | C$_2$H$_5$ | 3,4—(CH$_2$)$_3$— | n$_D^{25}$: 1.5797 |
| 1.2.4.7. | CH$_2$CF$_3$ | CH(CH$_3$)$_2$ | CH(CH$_3$)$_2$ | 3,4—(CH=CH)$_2$— | n$_D^{24}$: 1.5790 |
| 1.2.4.8. | CH[CH(CH$_3$)$_2$]$_2$ | CH(CH$_3$)$_2$ | CH(CH$_3$)$_2$ | 3,4—(CH=CH)$_2$— | n$_D^{24}$: 1.5837 |
| 1.2.4.9. | C$_{12}$H$_{25}$ | CH(CH$_3$)$_2$ | CH(CH$_3$)$_2$ | 3,4—(CH=CH)$_2$— | n$_D^{24}$: 1.5643 |
| 1.2.4.10. | C(CH$_3$)$_2$C$_2$H$_5$ | CH(CH$_3$)$_2$ | CH(CH$_3$)$_2$ | 3,4—(CH=CH)$_2$— | n$_D^{24}$: 1.5913 |
| 1.2.4.11. | Cyclopentyl | CH(CH$_3$)$_2$ | CH(CH$_3$)$_2$ | 3,4—(CH=CH)$_2$— | n$_D^{24}$: 1.6056 |
| 1.2.4.12. | C$_2$H$_5$ | CH(CH$_3$)$_2$ | CH(CH$_3$)$_2$ | 3,4—(CH=CH)$_2$— | n$_D^{24}$: 1.6098 |
| 1.2.4.13. | CH(CH$_3$)C$_2$H$_5$ | CH(CH$_3$)$_2$ | CH(CH$_3$)$_2$ | 3,4'(CH=CH)$_2$— | n$_D^{24}$: 1.5962 |
| 1.2.4.14. | CH(CH$_3$)$_2$ | C$_2$H$_5$ | Cyclopentyl | 3,4—(CH=CH)$_2$— | n$_D^{23}$: 1.6159 |
| 1.2.4.15. | C(CH$_3$)$_3$ | C$_2$H$_5$ | Cyclopentyl | 3,4—(CH=CH)$_2$— | n$_D^{23}$: 1.6081 |

EXAMPLE 2

Formulations for Active Ingredients of Formula I according to Preparation Examples 1.2

(throughout percentages are by weight)

| 2.1. Emulsifiable concentrates | (a) | (b) |
|---|---|---|
| active ingredient according to Preparation Examples 1.2. | 10% | 25% |
| calcium dodecylbenzenesulfonate | — | 5% |
| castor oil polyethylene glycol ether (36 moles of ethylene oxide) | 25% | 5% |
| cyclohexanone | — | 40% |
| butanol | 15% | — |
| xylene mixture | — | 25% |
| ethyl acetate | 50% | — |

Emulsions of any desired concentration can be produced from such concentrates by dilution with water.

| 2.2. Solutions | (a) | (b) |
|---|---|---|
| active ingredient according to Preparation Examples 1.2. | 10% | 5% |
| polyethylene glycol (mol. wt. 400) | 70% | — |
| N—methyl-2-pyrrolidone | 20% | 20% |
| epoxidised coconut oil | — | 1% |
| ligroin (boiling range 160–190° C.) | — | 74% |

These solutions are suitable for application in the form of microdrops.

| 2.3. Granulates | (a) | (b) |
|---|---|---|
| active ingredient according to Preparation Examples 1.2. | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier and the solvent is subsequently evaporated off in vacuo.

| 2.4. Extruder granulate | |
|---|---|
| active ingredient according to Preparation Examples 1.2. | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5. Coated granulate | |
|---|---|
| active ingredient according to Preparation Examples 1.2. | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.6. Dusts | (a) | (b) | (c) | (d) |
|---|---|---|---|---|
| active ingredient according to Preparation Examples 1.2. | 2% | 5% | 5% | 8% |
| highly dispersed silicic acid | 1% | 5% | — | — |
| talcum | 97% | — | 95% | — |
| kaolin | — | 90% | — | 92% |

Ready for use dusts are obtained by intimately mixing the active ingredient with the carriers and optionally grinding the mixture in a suitable mill.

| 2.7. Wettable powders | (a) | (b) | (c) |
|---|---|---|---|
| active ingredient according to Preparation Examples 1.2. | 20% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is ground in a suitable mill, affording wettable powders which can be diluted with water to give suspensions of any desired concentration.

| 2.8. Suspension concentrate | |
|---|---|
| active ingredient according to Preparation Examples 1.2. | 40% |
| ethylene glycol | 10% |
| nonylphenolpolyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3

Biological tests 3.1. Action against *Musca domestica*

A sugar cube is so moistened with a solution of the test compound that the concentration of active ingredient in the cube after drying is 500 ppm. The treated cube is placed on a dish together with a wet cotton wool swab and covered with a beaker. 10 adult one week-old, OP-resistant flies are placed under the beaker and kept at 25° C. and 50% humidity. The insecticidal action is determined after 24 hours by evaluating the mortality rate.

Compounds according to Examples 1.2. exhibit good activity in this test.

3.2. Action against *Lucilia sericata*

1 ml of an aqueous formulation containing 0.5% test compound is added at 50° C. to 9 ml of a culture medium. Then about 30 freshly hatched *Lucilia sericata* larvae are added to the culture medium, and the insecticidal action is determined after 48 to 96 hours by evaluating the mortality rate.

Compounds according to Examples 1.2. exhibit good activity against *Lucilia sericata* in this test.

3.3. Action against ticks in various stages of development 10 fresh *Boophilus microplus* females fully replete with blood are affixed in a row in the dorsal position to a PVC plate and covered with a cotton wool swab. 10 ml of the aqueous test solution are then poured over the test organisms. One hour later the cotton wool swab is removed and the ticks are dried overnight at 24° C. After drying, the ticks are kept at 28° C. and 80% humidity for 4 weeks until oviposition has taken place and the larvae have started to hatch.

Each test compound is tested in a concentration of 500 ppm. The acaricidal action manifests itself in the females as mortality or sterility or in the egg deposits as the blocking of embryogenesis or the act of hatching. All the compounds are tested against two different tick species, the OP-resistant BIARRA strain and the amidine-resistant ULAM strain.

Compounds according to Example 1.2. exhibit good activity in the above test.

3.4. Insecticidal stomach poison action against *Spodoptera littoralis* larvae ($L_1$)

Cotton plants in the cotyledon stage are sprayed with an aqueous emulsion (obtained from a 10% emulsifiable concentrate) containing 400 ppm of the test compound.

After the coating has dried, each cotton plant is populated with *Spodoptera littoralis* larvae in the first larval stage. The test is carried out at 26° C. and about 50% relative humidity. Mortality is assessed after 2 and 3 days, and defects in the development and sloughing of the developed larvae are assessed after 5 days.

Compounds according to Examples 1.2. exhibit good activity in this test.

3.5. Insecticidal stomach poison action against *Spodoptera littoralis* and *Heliothis virescens* larvae ($L_3$)

Potted soybean plants (pot size: 10 cm diameter) in the 4-leaf stage are sprayed with aqueous emulsions containing the test compound in a concentration of 400 ppm.

After 2 days the treated soybean plants are populated with 10 larvae of *Spodoptera littoralis* and 10 larvae of *Heliothis virescens* in the third larval stage. The test is carried out at 26° C. and about 60% relative humidity in dim light. After 2 and 5 days evaluation is made to determine the percentage mortality of the larvae.

Compounds according to Examples 1.2. are 80–100% effective (mortality).

3.6. Insecticidal stomach poison action against *Plutella xylostella* and *Crocidolomia binotalis* larvae ($L_2$)

Potted Chinese cabbage plants (pot size: 10 cm diameter) in the 4-leaf stage are sprayed with aqueous emulsions containing the test compound in a concentration of 400 ppm.

After 2 days, each treated Chinese cabbage plant is populated with 10 *Plutella xylostella* or *Crocidolomia binotalis* larvae in the $L_2$ stage. The test is carried out at 26° C. and about 60% relative humidity in dim light. After 2 and 5 days evaluation is made to determine the percentage mortality of the larvae.

Compounds according to Examples 1.2. are 80–100% effective (mortality).

3.7. Contact action against *Nilaparvata lugens* (nymphs)

The test is carried out with growing plants. For this purpose rice plants about 20 days old and about 15 cm in height are planted into pots (diameter 5.5 cm).

The plants are each sprayed on a rotary table with 40 ml of an acetonic solution containing 400 ppm of the test compound. After the spray-coating has dried, each plant is populated with 20 nymphs of the test organisms in the second or third stage. In order to prevent the cicadas from escaping, a plexiglass cylinder is slipped over each of the populated plants and sealed with a gauze top. The nymphs are kept for 6 days on the treated plants which have to be resprayed at least once. The test is carried out at a temperature of about 23° C. and at 55% relative humidity and the plants are exposed to light for a period of 16 hours per day.

Compounds according to Examples 1.2. exhibit good activity in this test.

3.8. Systemic action against *Nilaparvata lugens*

Rice plants about 10 days old (about 10 cm in height) are placed in a plastic beaker which contains 20 ml of an aqueous emulsion formulation of the test compound in a concentration of 100 ppm and which is closed by a perforated plastic lid. The roots of each rice plant are pushed through a hole in the plastic lid into the aqueous test formulation. The hole is sealed with cotton wool to fix the plant and to exclude the effect of the gas phase from the test formulation. Each rice plant is then populated with 20 nymphs of *Nilaparvata lugens* in the $N_2$ to $N_3$ stage and is covered with a plastic cylinder. The test is carried out at 26° C. and about 60% relative humidity and the plants are exposed to light for a period of 16 hours per day. After 2 and 5 days a count is made of the number of test organisms killed in comparison with untreated controls, thereby establishing whether the test compound absorbed via the roots kills the test organisms on the upper parts of the plants.

Compounds according to Examples 1.2. are 80–100% effective (mortality) against *Nilaparvata lugens* in this test.

3.9. Action against soil insects (*Diabrotica balteata*)

350 ml of soil (consisting of 95% by volume sand and 5% by volume peat) are mixed with 150 ml of each of a number of emulsion formulations containing the test compound in a concentration of 400 ppm. Then plastic beakers having an upper diameter of about 10 cm are partly filled with the treated soil. Ten larvae of *Diabrotica balteata* in the third larval stage are used and four maize seedlings are planted per beaker and the beakers are filled with soil. The filled beakers are covered with plastic film and kept at a temperature of about 24° C. and a relative humidity of about 50%. Six days after the start of the test, the soil contained in the beakers is sieved and the mortality of the larvae that remain is assessed.

Compounds according to Examples 1.2. exhibit good activity in this test.

3.10. Contact action against *Aphis craccivora*

Before the start of the test, 4–5 day-old pea seedlings (*Pisum sativum*) raised in pots are each populated with about 200 insects of the species *Aphis craccivora*. The treated plants are sprayed direct to drip point 24 hours later with an aqueous formulation containing 400 ppm of the test compound. Two plants are used for each test compound. A mortality count is made after 3 and 5 days. The test is carried out at about 21° C. and a relative humidity of about 55%.

Compounds according to Examples 1.2. exhibit good activity in this test.

3.11. Contact action against *Myzus persicae*

Before the start of the test, pea seedlings (*Pisum sativum*) about 4–5 days old and raised in water are each populated with about 200 insects of the species *Myzus persicae*. The treated plants are sprayed direct to drip point 24 hours later with an aqueous suspension containing 100 ppm of the test compound. Two plants are used for each test compound. A mortality count is made 3 and 5 days after application. The test is carried out at about 21° C. and about 60% relative humidity.

Compounds according to Examples 1.2. exhibit good activity in this test.

3.12. Action against *Tetranychus urticae* (OP-sensitive)

24 hours before the test for acaricidal action, the primary leaves of *Phaseolus vulgaris* plants are infected with an infested piece of leaf from a mass culture of *Tetranychus urticae* (OP-sensitive) (mixed population). The tolerance refers to diazinone.

The treated infested plants are sprayed to drip point with a test solution in emulsion form containing 400 ppm of the test compound. During the test run the plants are kept in greenhouse compartments at about 25° C. and about 50% relative humidity.

After 6 days, a count of the number of living and dead imagines and larvae (all mobile stages) and egg deposits is made under a steroscopic microscope.

Compounds according to Examples 1.2. exhibit good activity in this test.

3.13. Action against *Panonychus ulmi* (OP- and carbamate-resistant)

Apple seedlings having about 20–30 leaves, in pots, are each populated with 60 adult *Panonychus ulmi* females. After 7 days the infested plants are sprayed to drip point with an aqueous emulsion containing 100 ppm of the test compound. The treated plants are then kept in a greenhouse for 14 days at about 25° C. and about 50% relative humidity.

After this time, the test is evaluated by detaching 20 leaves from each plant, removing the mite population from the detached leaves using a brushing-off device and counting the eggs, post-embryonic stages and adults under a stereoscopic microscope. The percentage reduction in the mite population is evaluated in comparison with untreated controls.

Compounds according to Examples 1.2. exhibit good activity in this test.

3.14. Action against *Anthonomus grandis* (adults)

Two cotton plants in the 6-leaf stage, in pots, are each sprayed with wettable aqueous emulsion formulations containing 100 ppm of the test compound. After the spray-coating has dried (about 1.5 hours) each plant is populated with 10 adult beetles (*Anthonomus grandis*). Plastic cylinders, covered at the top with gauze, are then slipped over the treated plants populated with the test insects to prevent the beetles from migrating from the plants. The treated plants are kept at 25° C. and about 60% relative humidity. Evaluation is made after 2, 3, 4 and 5 days to determine the percentage mortality of the beetles (percentage in dorsal position) and the anti-feeding action as compared with untreated controls.

Compounds according to Examples 1.2. exhibit good activity in this test.

3.15. Action against *Dermanyssus gallinae*

2 to 3 ml of a solution containing 100 ppm of the test compound and about 200 mites in various development stages are placed in a glass container open at the top. The container is then closed with a cotton wool plug, shaken for 10 minutes until the mites are completely wet and then briefly inverted in order that the remaining test solution can be absorbed by the cotton wool. After 3 days the percentage mortality of the mites is determined by counting the dead insects.

Compounds according to Examples 1.2. are 80–100% effective (mortality).

We claim:

1. A compound of formula I

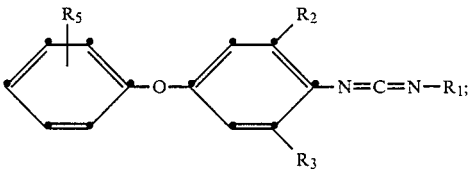

in which
$R_1$ represents $C_1$–$C_{12}$alkyl, $C_1$–$C_{12}$alkyl mono- or poly-substituted by halogen and/or by $C_1$–$C_6$alkoxy, $C_3$–$C_8$cycloalkyl, $C_3$–$C_8$cycloalkyl mono- or poly-substituted by $C_1$–$C_3$alkyl, or $C_3$–$C_8$cycloalkyl-$C_1$–$C_4$alkyl;
$R_2$ represents hydrogen or $C_1$–$C_5$alkyl;
$R_3$ represents $C_1$–$C_5$alkyl or $C_5$–$C_6$cycloalkyl;
$R_4$ represents hydrogen or methyl;
$R_5$ represents a $-(CH=CH)_2$, $-(CH_2)_3$ or $-(CH_2)_4$ bridge in the 2,3- or 3,4-position;
and the salts thereof with organic or inorganic acids.

2. A compound of formula I according to claim 1 in which $R_1$ represents $C_1$-$C_8$alkyl, $C_1$-$C_8$alkyl mono- or poly-substituted by halogen and/or by $C_1$-$C_5$alkoxy, or $C_3$-$C_8$cycloalkyl, $R_2$ represents $C_1$-$C_5$alkyl; $R_3$ represents $C_1$-$C_5$alkyl or cyclopentyl; $R_4$ represents hydrogen; and $R_5$ represents a $-(CH=CH-)_2$, $-(CH_2-)_3$ or $-(CH_2-)_4$ bridge in the 2,3- or 3,4-position.

3. A compound of formula I according to claim 2 in which $R_1$ represents $C_1$-$C_4$alkyl; $R_2$ and $R_3$ each represents $C_1$-$C_3$alkyl; $R_4$ represents hydrogen; $R_5$ represents a $-(CH=CH-)_2$ or $-(CH_2-)_3$ bridge in the 3,4-position.

4. The compounds according to claim 1 of the formulae:

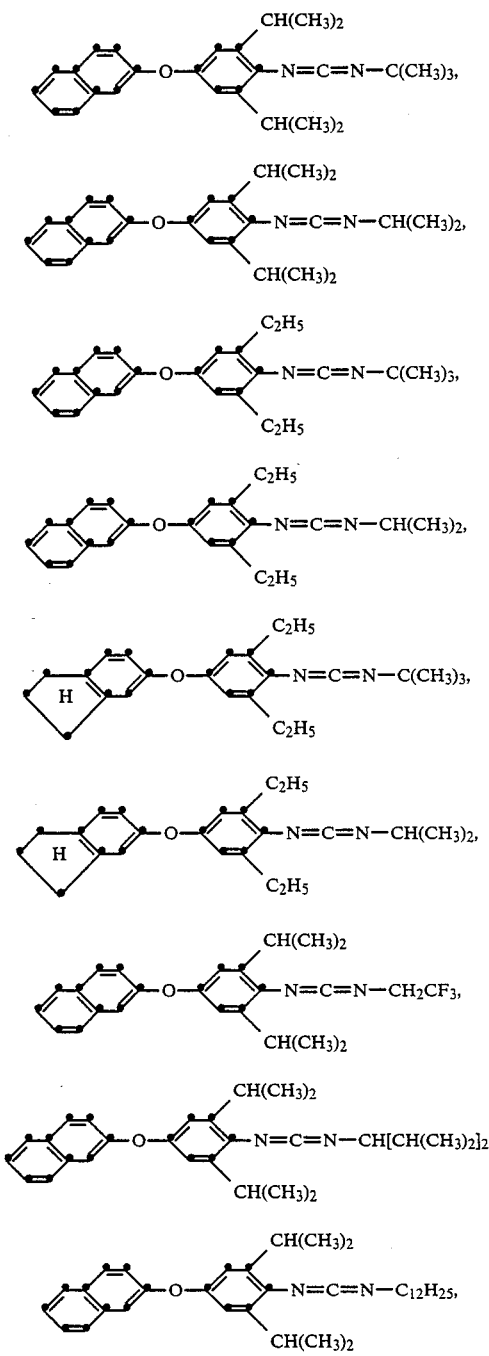

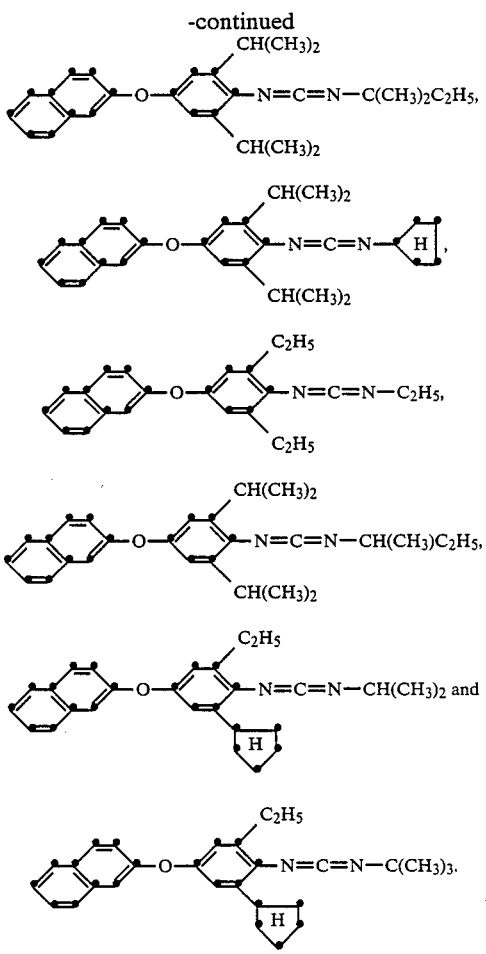

5. A pesticidal composition containing as active ingredient an insecticidally and acaracidally effective amount of a

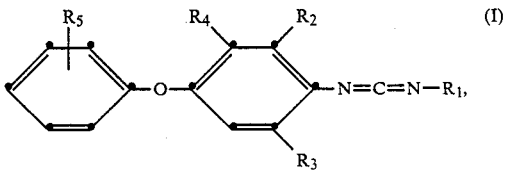

in which
$R_1$ represents $C_1$-$C_{12}$alkyl, $C_1$-$C_{12}$alkyl mono- or poly-substituted by halogen and/or by $C_1$-$C_6$alkoxy, $C_3$-$C_8$cycloalkyl, $C_3$-$C_8$cycloalkyl mono- or poly-substituted by $C_1$-$C_3$alkyl, or $C_3$-$C_8$cycloalkyl-$C_1$-$C_4$alkyl;
$R_2$ represents hydrogen or $C_1$-$C_5$alkyl;
$R_3$ represents $C_1$-$C_5$alkyl or $C_5$-$C_6$cycloalkyl;
$R_4$ represents hydrogen or methyl;
$R_5$ represents a $-(CH=CH-)_2$, $-(CH_2-)_3$ or $-(CH_2-)_4$ bridge in the 2,3- or 3,4-position;
or a salt thereof with an organic or inorganic acid together with a pesticidally suitable carrier or adjuvant.

6. A pesticidal composition according to claim 5 containing as active ingredient a compound of formula I in which $R_1$ represents $C_1$-$C_8$alkyl, $C_1$-$C_8$alkyl mono- or poly-substituted by halogen and/or by $C_1$-$C_5$alkoxy, or $C_3$-$C_8$cycloalkyl, $R_2$ represents $C_1$-$C_5$alkyl; $R_3$ represents $C_1$–$C_5$alkyl or cyclopentyl; $R_4$ represents hydrogen; $R_5$ represents a $+CH=CH+_2$, $+CH_2+_3$ or $+CH_2+_4$ bridge in the 2,3- or 3,4-position.

7. A pesticidal composition according to claim 6 in which $R_1$ represents $C_1$–$C_4$alkyl; $R_2$ and $R_3$ each represents $C_1$–$C_3$alkyl; $R_4$ represents hydrogen; $R_5$ represents a or $+CH=CH+_2$ or $+CH_2+_3$ bridge in the 3,4-position.

8. A method of controlling pests in and on animals and plants, characterised in that the pests in various stages of development are brought into contact with a compound of formula I

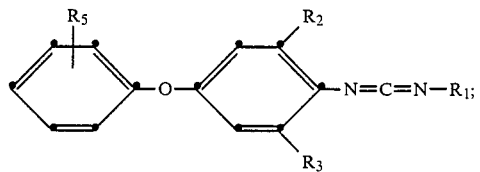

in which
$R_1$ represents $C_1$–$C_{12}$alkyl, $C_1$–$C_{12}$alkyl mono- poly-substituted by halogen and/or by $C_1$–$C_6$alkoxy, $C_3$—$C_8$cycloalkyl, $C_3$–$C_8$cycloalkyl mono- or poly-substituted by $C_1$–$C_3$alkyl, or $C_3$–$C_8$cycloalkyl-$C_1$–$C_4$alkyl;
$R_2$ represents hydrogen or $C_1$–$C_5$alkyl;
$R_3$ represents $C_1$–$C_5$alkyl or $C_5$–$C_6$cycloalkyl;
$R_4$ represents hydrogen or methyl;
$R_5$ represents a $+CH=CH+_2$, $+CH_2+_3$ or $+CH_2+_4$ bridge in the 2,3- or 3,4-position
or with a salts thereof with an organic or inorganic acid.

9. Method according to claim 8 for controlling insects and arachnids.

* * * * *